US009255098B2

(12) United States Patent
Wang et al.

(10) Patent No.: US 9,255,098 B2
(45) Date of Patent: Feb. 9, 2016

(54) XANTHINE DERIVATIVE

(71) Applicant: Chengdu Easton Pharmaceutical Co., Ltd., Chengdu (CN)

(72) Inventors: Ying Wang, Chengdu (CN); Yongzhe Xiang, Chengdu (CN); Guodong Cen, Chengdu (CN); Long Huang, Chengdu (CN); Jian Liu, Chengdu (CN); Ning Zhou, Chengdu (CN); Jibing Zhang, Chengdu (CN)

(73) Assignee: Chengdu Easton Pharmaceutical Co., Ltd., Chengdu (CN)

( * ) Notice: Subject to any disclaimer, the term of this patent is extended or adjusted under 35 U.S.C. 154(b) by 0 days.

(21) Appl. No.: 14/409,952

(22) PCT Filed: May 15, 2013

(86) PCT No.: PCT/CN2013/075627
§ 371 (c)(1),
(2) Date: Dec. 19, 2014

(87) PCT Pub. No.: WO2013/189219
PCT Pub. Date: Dec. 27, 2013

(65) Prior Publication Data
US 2015/0183788 A1    Jul. 2, 2015

(30) Foreign Application Priority Data

Jun. 20, 2012 (CN) .......................... 2012 1 0205678

(51) Int. Cl.
| | |
|---|---|
| *A61K 31/522* | (2006.01) |
| *C07D 473/08* | (2006.01) |
| *A61K 31/437* | (2006.01) |
| *C07D 473/06* | (2006.01) |

(52) U.S. Cl.
CPC ............ *C07D 473/08* (2013.01); *A61K 31/437* (2013.01); *A61K 31/522* (2013.01); *C07D 473/06* (2013.01)

(58) Field of Classification Search
CPC ........................ C07D 473/04; C07D 473/08
See application file for complete search history.

(56) References Cited

U.S. PATENT DOCUMENTS

| | | | |
|---|---|---|---|
| 7,407,955 B2 | 8/2008 | Himmelsbach et al. | |
| 7,888,343 B2 | 2/2011 | Schoenafinger et al. | |
| 8,119,648 B2 | 2/2012 | Himmelsbach et al. | |
| 8,178,541 B2 | 5/2012 | Himmelsbach et al. | |
| 2002/0198205 A1 | 12/2002 | Himmelsbach et al. | |
| 2004/0077645 A1 | 4/2004 | Himmelsbach et al. | |
| 2004/0087587 A1 | 5/2004 | Himmelsbach et al. | |
| 2004/0097510 A1 | 5/2004 | Himmelsbach et al. | |
| 2006/0205711 A1 | 9/2006 | Himmelsbach et al. | |
| 2006/0247226 A1 | 11/2006 | Himmelsbach et al. | |
| 2007/0197563 A1 | 8/2007 | Schoenafinger et al. | |
| 2008/0249089 A1 | 10/2008 | Himmelsbach et al. | |
| 2008/0255159 A1 | 10/2008 | Himmelsbach et al. | |
| 2010/0173916 A1 | 7/2010 | Himmelsbach et al. | |
| 2010/0204250 A1 | 8/2010 | Himmelsbach et al. | |
| 2011/0144083 A1 | 6/2011 | Himmelsbach et al. | |
| 2011/0144095 A1 | 6/2011 | Himmelsbach et al. | |
| 2012/0035158 A1 | 2/2012 | Himmelsbach et al. | |
| 2012/0040982 A1 | 2/2012 | Himmelsbach et al. | |
| 2012/0208831 A1 | 8/2012 | Himmelsbach et al. | |
| 2012/0252782 A1 | 10/2012 | Himmelsbach et al. | |
| 2012/0252783 A1 | 10/2012 | Himmelsbach et al. | |

FOREIGN PATENT DOCUMENTS

| | | | | |
|---|---|---|---|---|
| CA | 2496249 A1 | * | 3/2004 | .......... C07D 473/04 |
| CN | 1492870 | | 4/2004 | |
| CN | 1675212 | | 9/2008 | |

OTHER PUBLICATIONS

Weber, Ann. Burger's Medicinal Chemistry, Drug Discovery, and Development, Seventh Edition. 2010. 1-37.*
International Search Report mailed Aug. 22, 2013 which issued in corresponding International Patent Application No. PCT/CN2013/075627 (12 pages).

* cited by examiner

*Primary Examiner* — Golam M M Shameem
*Assistant Examiner* — Laura Daniel
(74) *Attorney, Agent, or Firm* — Nixon Peabody LLP

(57) ABSTRACT

The present invention discloses a xanthine derivative having the structure of the following general formula (I) or a pharmaceutically acceptable salt thereof; further discloses a preparation method for the xanthine derivative or a pharmaceutically acceptable salt thereof; and further discloses the use of the xanthine derivative or a pharmaceutically acceptable salt thereof. Through experiments of DPP-IV activity inhibition experiments in vitro, impact on glucose tolerance in normal mice and impact on blood glucose in spontaneous diabetic mice, it proves that the compounds and pharmaceutically acceptable salts thereof show good DPP-IV inhibition activity, can be applied to prepare medicines for treating dipeptidyl peptidase IV-related diseases, and more particularly, can be applied to the use of medicines for treating type II diabetes or diseases of abnormal glucose tolerance.

(I)

17 Claims, No Drawings

XANTHINE DERIVATIVE

CROSS-REFERENCE TO RELATED APPLICATIONS

This application is an U.S. national stage of PCT/CN2013/075627, filed on May 15, 2013 which claims priority to Chinese Patent Application No. 201210205678.4, filed on Jun. 20, 2012, the contents of which are each incorporated herein by reference in its entirety.

FIELD OF THE INVENTION

The present invention relates to the field of pharmaceutical chemistry, specifically to a class of substituted xanthine derivatives, preparation method and the use thereof as therapeutic agents, especially as dipeptidyl peptidase IV (DPP-IV) inhibitors.

BACKGROUND OF THE INVENTION

Diabetes is a multi-cause metabolic disease, which is characterized by chronic high blood glucose, accompanied by sugar, fat and protein metabolism disorder caused by the defect of insulin secretion and/or action. Diabetes is also a very old disease, which is due to the relative or absolute lack of insulin in the human body, causing the increased concentration of blood glucose, resulting in sugar discharged in a large amount with the urine, and accompanied by polydipsia, polyuria, polyphagia, weight loss, dizziness, fatigue and other symptoms.

In the treatment of diabetes, exercise therapy and diet therapy are two essential treatments of diabetes. When these two treatments are not sufficient to control the disease condition, insulin or oral hypoglycemic agents can be used. However, since these existing hypoglycemic agents have too many side effects, it is particularly important to develop a novel drug with less side effects and more therapeutic effects in the treatment of diabetes.

Dipeptidyl peptidase IV (DPP-IV) is a serine protease, which can selectively cleave the N-terminus dipeptide of the peptide chain containing one proline residue at the penultimate position from the N-terminal. Although the physiological effect of DPP-IV on mammals has not been fully confirmed, it plays an important role in neuropeptide metabolism, T-cell activation, adhesion of cancer cells and endothelium, process of HIV virus coming into lymphocytes, and other processes (see WO 98/19998).

Studies have shown that, DPP-IV can degrade glucagon-like peptide (GLP-1), i.e., by cleaving the histidine-alanine dipeptide at N-terminal of GLP-1, the GLP-1 in its active form can be degraded into inactive GLP-1-(7-36) amide, which is further degraded into inactive GLP-1-(9-36) amide (see, Hansen L, Deacon C F, Ørskov C, et al., Endocrinology, 1999, 140: 5356-5363). In physiological conditions, the half-life of intact GLP-1 in circulatory blood is very short, and the inactive metabolites obtained from the degradation of GLP-1 by DPP-IV can bind with the GLP-1 receptor to antagonize the active GLP-1, so as to shorten the physiological responses of GLP 1 receptor to GLP-1, while the DPP-IV inhibitors can completely protect endogenous, even exogenous GLP-1 from being inactivated by DPP-IV, and thus greatly increase the physiology activity of GLP-1 (by 5-10 times). GLP-1 is an important stimulus to the secretion of pancreatic insulin and can directly influence the distribution of glucose, therefore, DPP-IV inhibitors play a very positive role in the treatment of patients with non-insulin-dependent diabetes (U.S. Pat. No. 6,110,949).

SUMMARY OF THE INVENTION

The present invention relates to the substituted xanthine derivatives, as well as preparation method and medical application thereof, especially the substituted xanthine derivatives as represented by the general formula (I) or a pharmaceutically acceptable salt thereof, and to the use thereof in preparing a medicament for the treatment of the DPP-IV related diseases. More specifically, said use is in preparing a medicament for the treatment of type II diabetes or diseases of abnormal glucose tolerance. One object of the present invention is to provide a substituted xanthine derivative having the structure as shown in the following general formula (I) or a pharmaceutically acceptable salt thereof:

(I)

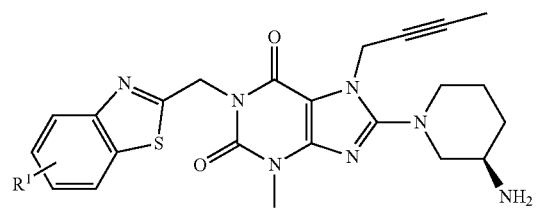

Wherein: $R^1$ is selected from hydrogen atom, fluorine atom, chlorine atom, bromine atom, iodine atom or cyano group.

Wherein, $R^1$ is preferably a substituent at the 5-position of (1,3-benzothiazol-2-yl)methyl, and $R^1$ is further preferably selected from hydrogen atom, fluorine atom or chlorine atom.

The substituted xanthine derivative of the present invention preferably has the structure as shown in the following general formula (II):

(II)

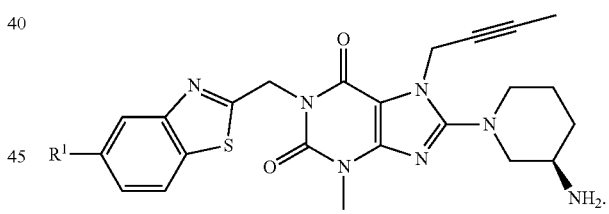

Wherein, $R^1$ is selected from hydrogen atom, fluorine atom or chlorine atom.

Particularly preferably, the substituted xanthine derivative of the present invention is the following compound:

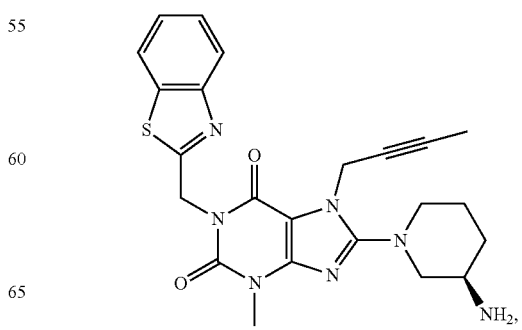

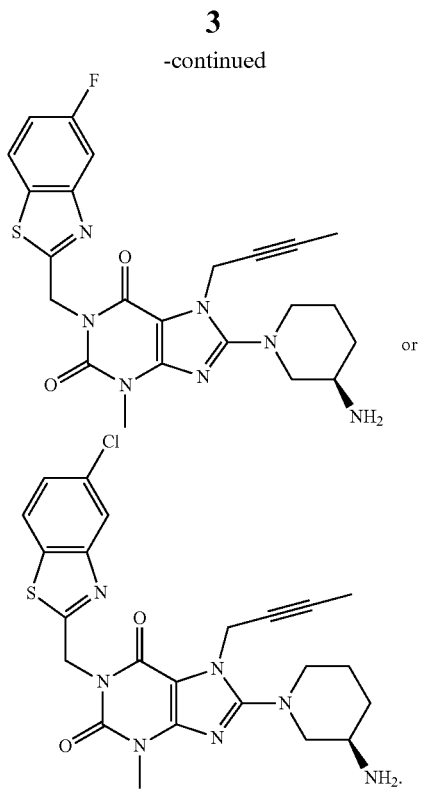

Pharmaceutically acceptable salts of the present invention are the salts formed by the compounds of the present invention and the acids selected from the following: hydrochloric acid, p-toluenesulfonic acid, tartaric acid, maleic acid, lactic acid, methanesulfonic acid, sulfuric acid, phosphoric acid, citric acid, acetic acid or trifluoroacetic acid; and preferably the acid is hydrochloric acid, p-toluenesulfonic acid, trifluoroacetic acid or tartaric acid.

More specifically, the substituted xanthine derivatives of the present invention or the pharmaceutically acceptable salts thereof are:

1-[(5-fluoro-1,3-benzothiazol-2-yl)methyl]-3-methyl-7-(2-butyn-1-yl)-8-[(R)-3-amino-piperidin-1-yl]-xanthine;
1-[(1,3-benzothiazol-2-yl)methyl]-3-methyl-7-(2-butyn-1-yl)-8-[(R)-3-amino-piperidin-1-yl]-xanthine;
1-[(5-chloro-1,3-benzothiazol-2-yl)methyl]-3-methyl-7-(2-butyn-1-yl)-8-[(R)-3-amino-piperidin-1-yl]-xanthine;
1-[(5-fluoro-1,3-benzothiazol-2-yl)methyl]-3-methyl-7-(2-butyn-1-yl)-8-[(R)-3-amino-piperidin-1-yl]-xanthine hydrochloride;
1-[(1,3-benzothiazol-2-yl)methyl]-3-methyl-7-(2-butyn-1-yl)-8-[(R)-3-amino-piperidin-1-yl]-xanthine hydrochloride.

Another object of the present invention is to provide a preparation method of the above substituted xanthine derivatives or a pharmaceutically acceptable salt thereof, comprising the following steps:

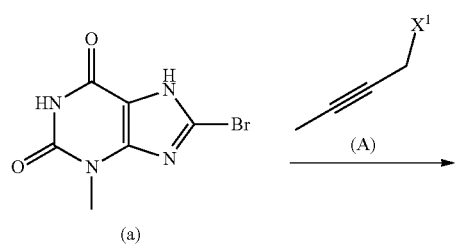

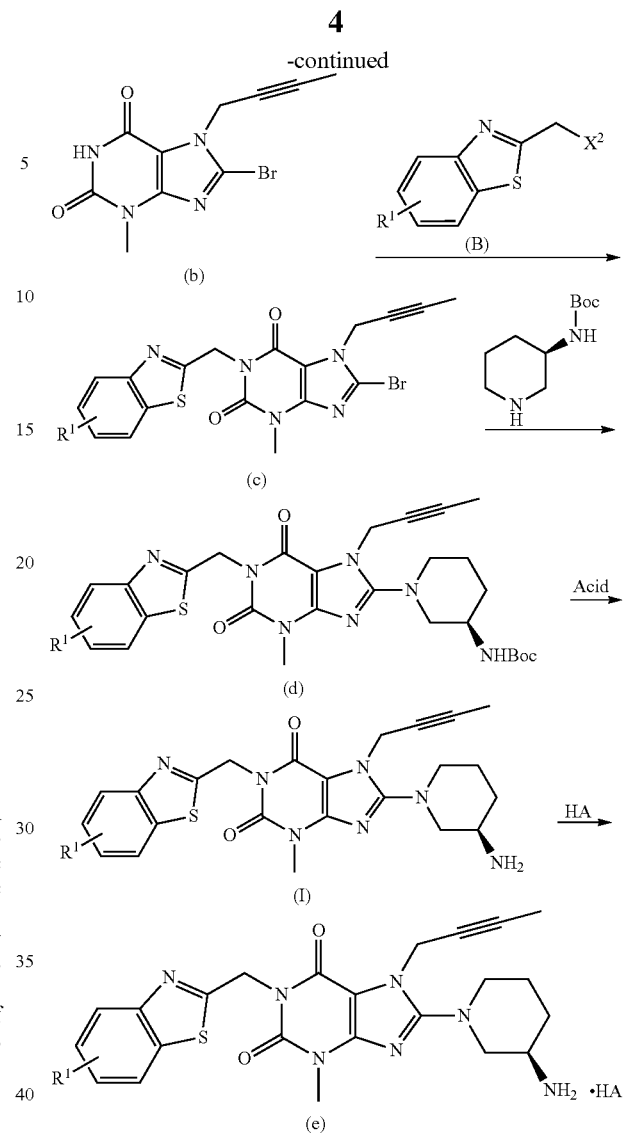

At room temperature (10~25° C.), the starting raw material a is reacted with the raw material A; the generated intermediate b is further subjected to a substitution reaction with the raw material B to generate the intermediate c; the intermediate c and (R)-3-tert-butoxycarbonyl aminopiperidine are reacted under the heating condition (50~100° C.) to generate the intermediate d; the intermediate d is subjected to deprotection under acidic condition, to obtain the target compound I as a free base; and optionally, the target compound I is further reacted with an acid to prepare the corresponding salt e.

Wherein, in the raw material A, $X^1$ is a leaving group, and said $X^1$ is preferably Cl, Br or I; wherein, in the raw material B, $X^2$ is a leaving group, and said $X^2$ is preferably Cl, Br or I; the acid used for removing the protecting group Boc is preferably hydrochloric acid or trifluoroacetic acid.

Another object of the present invention is to provide the use of the above-described substituted xanthine derivatives or a pharmaceutically acceptable salt thereof as therapeutic agent, particularly as the active inhibitor of the DPP-IV in the field of medicine.

Specifically, the present invention relates to the use of the above substituted xanthine derivatives or a pharmaceutically acceptable salt thereof in preparing the medicament for the treatment of DPP-IV related diseases. More specifically, the present invention relates to the use of the above substituted xanthine derivatives or a pharmaceutically acceptable salt thereof in preparing the medicament for the treatment of type II diabetes or diseases of abnormal glucose tolerance.

DETAILED DESCRIPTION

The present invention will be described in further details with the examples, but does not intend to limit the protect scope of the present invention, while any equivalent in this field in accordance with the disclosure of the present invention falls within the scope of the present invention.

Structures of compounds are verified by mass spectrometry (MS) or the nuclear magnetic resonance ($^1$H NMR). Displacement ($\delta$) of the nuclear magnetic resonance ($^1$H NMR) is given in a unit of parts per million (ppm); measurement by nuclear magnetic resonance ($^1$H NMR) is carried out on Bruker AVANCE-300 NMR instrument, wherein the measuring solvent is hexadeuterated dimethyl sulfoxide (DMSO-$d_6$), and the internal standard is tetramethyl silane (TMS).

Measurement by mass spectrum (MS) is carried out on FINNIGAN LCQAd (ESI) mass spectrometer (manufacturer: Therm, type: Finnigan LCQ advantage MAX).

$IC_{50}$ values are determined by envision (PerkinElmer Corporation).

Yantai Huanghai HSGF254 or Qingdao GF254 silica gel plate is used as the thin layer silica gel.

Unless otherwise specified, the reactions mentioned in the present invention are carried out under the nitrogen atmosphere.

In the present invention, the term "nitrogen atmosphere" refers, for example, to connecting the reaction flask to a nitrogen balloon with 1 L volume.

Unless otherwise specified, the solutions mentioned in the reaction of the present invention refer to the aqueous solutions.

In the present invention, the term "room temperature" refers to the temperature between 10° C. and 25° C.

In one embodiment, the present invention relates to the substituted xanthine derivatives having the structure represented by the general formula (I), or a pharmaceutically acceptable salt thereof:

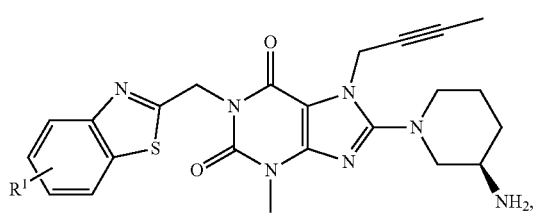

(I)

Wherein, $R^1$ is selected from hydrogen atom, fluorine atom, chlorine atom, bromine atom, iodine atom or cyano group, and $R^1$ is preferably at the 5-position of (1,3-benzothiazol-2-yl)methyl, and $R^1$ is further preferably selected from hydrogen atom, fluorine atom or chlorine atom.

In a preferred embodiment, the abovementioned pharmaceutically acceptable salts are formed by the substituted xanthine derivatives of the present invention and one or more acids selected from the following acids: hydrochloric acid, p-toluenesulfonic acid, tartaric acid, maleic acid, lactic acid, methanesulfonic acid, sulfuric acid, phosphoric acid, citric acid, acetic acid or trifluoroacetic acid. More preferably, the acid is selected from hydrochloric acid, p-toluenesulfonic acid, trifluoroacetic acid, tartaric acid or mixtures thereof.

In a further preferred embodiment, the substituted xanthine derivative of the present invention or a pharmaceutically acceptable salt thereof is selected from:

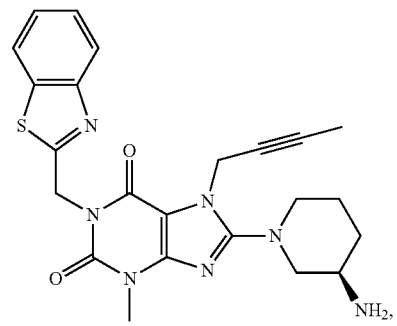

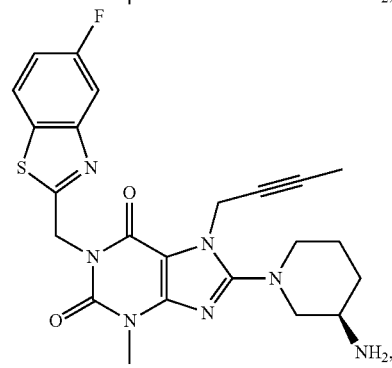

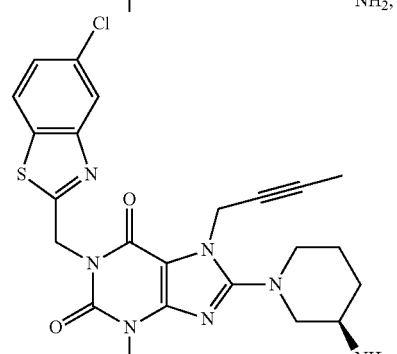

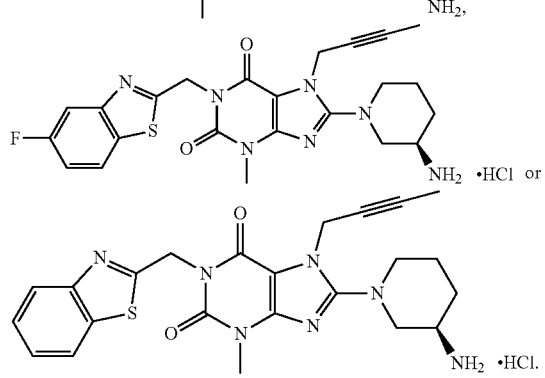

In another embodiment, the present invention relates to the preparation method of the substituted xanthine derivatives having the structure represented by the following general formula (I) or a pharmaceutically acceptable salt thereof, wherein the method comprises the following steps:

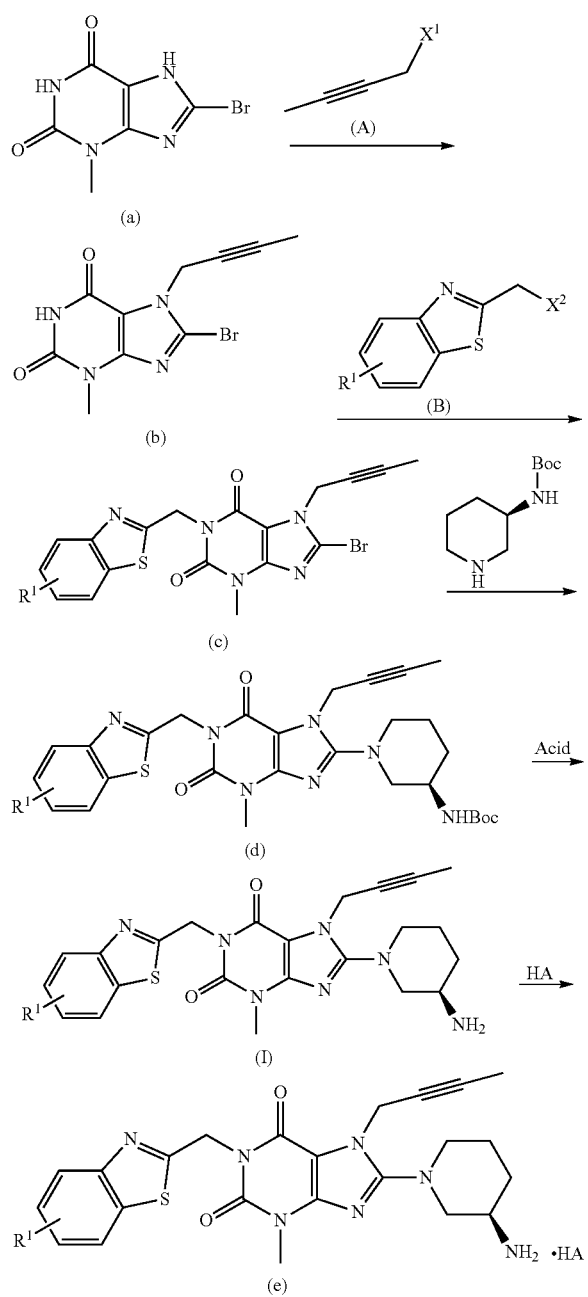

At room temperature, the raw material a is reacted overnight with the raw material A in N,N-dimethylformamide; after the reaction is completed, the obtained reaction solution is poured into water, suction filtrated, washed with water and dried to obtain the intermediate b; wherein $X^1$ in the raw material A is a leaving group, and said $X^1$ is preferably Cl, Br or I;

The obtained intermediate b is reacted overnight with the raw material B and a base in N,N-dimethylformamide at room temperature; after the reaction is completed, the obtained reaction mixture is poured into water, suction filtrated, washed with water and dried to give the intermediate c; wherein $X^2$ in the raw material B is a leaving group, said $X^2$ is preferably Cl, Br or I; wherein the base is preferably potassium carbonate, sodium carbonate, sodium hydroxide or sodium hydride;

The obtained intermediate c is reacted with (R)-3-tert-butoxycarbonyl-aminopiperidine and a base in N,N-dimethylformamide under heating conditions (50~100° C.) for 2~8 h; after the reaction solution is cooled to room temperature, the obtained reaction solution is poured into water, suction filtrated, washed with water and dried to give the intermediate d; wherein the base is preferably potassium carbonate, sodium carbonate, sodium hydroxide or sodium hydride;

The obtained intermediate d is reacted with an acid in an organic solvent at room temperature for 2~10 h; after the reaction is completed, the pH of the residue solution is adjusted to 7-8 with potassium carbonate aqueous solution, and then, extracted by the organic solvent; the obtained organic phase is dried, filtered and concentrated to give the crude product; the crude product is further purified by chromatography, so as to give the target compound I; wherein the acid used for removing the protecting group Boc is preferably hydrochloric acid or trifluoroacetic acid; the used organic solvent is preferably dichloromethane, chloroform, ethyl acetate or tetrahydrofuran; and Optionally, (5) the obtained target compound I is reacted with an acid solution in an organic solvent, and stirred for an appropriate time; then the solvent is evaporated, and the residue is washed and dried, so as to give the corresponding salt e; wherein the used organic solvent is preferably dichloromethane, chloroform, ethyl acetate or tetrahydrofuran.

In another embodiment, the present invention relates to the use of the above substituted xanthine derivatives or a pharmaceutically acceptable salt thereof in preparing the medicament for the treatment of DPP-IV related diseases.

In a preferred embodiment, the present invention relates to the use of the above substituted xanthine derivatives or a pharmaceutically acceptable salt thereof in preparing the medicament for the treatment of type II diabetes or diseases of abnormal glucose tolerance.

EXAMPLES

Example 1

Preparation of 1-[(5-fluoro-1,3-benzothiazol-2-yl)methyl]-3-methyl-7-(2-butyn-1-yl)-8-[(R)-3-amino-piperidin-1-yl]-xanthine

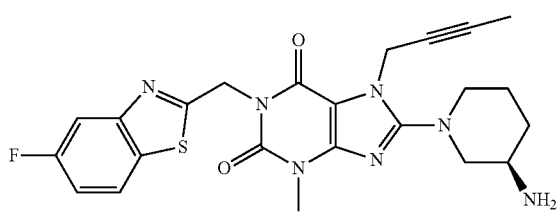 [SMILES: CC#CCn1c(N2CCC[C@@H](N)C2)nc2c1c(=O)n(Cc1nc3cc(F)ccc3s1)c(=O)n2C]

Preparation scheme is shown below:

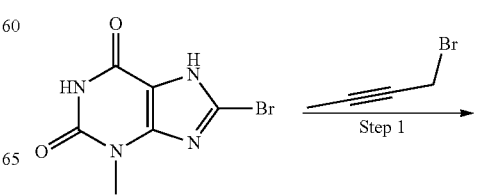

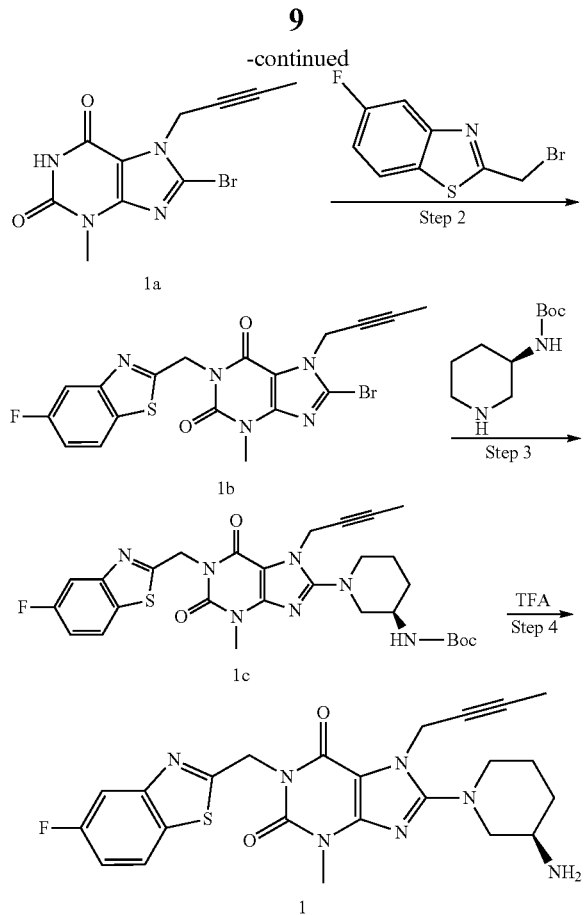

Step 3: preparation of 1-[(5-fluoro-1,3-benzothiazol-2-yl)methyl]-3-methyl-7-(2-butyn-1-yl)-8-[(R)-3-tert-butoxycarbonyl-aminopiperidin-1-yl]-xanthine By utilizing the well known method, 1-[(5-fluoro-1,3-benzothiazol-2-yl)methyl]-3-methyl-7-(2-butyn-1-yl)-8-bromo-xanthine 1b (240 mg, 0.51 mmol) was dissolved in N,N-dimethylformamide (5 ml). (R)-3-tert-butoxycarbonyl-aminopiperidine (130 mg, 0.66 mmol) and potassium carbonate (107 mg, 0.78 mmol) were added to give a reaction mixture. The reaction mixture was reacted at 75° C. for 2 hours, and TLC was used to monitor the reaction progress. After the reaction was completed, the obtained reaction mixture was cooled to room temperature. The cooled reaction solution was poured into cool water, suction filtered, and the obtained solid was washed with water, dried to give 1-[(5-fluoro-1,3-benzothiazol-2-yl)methyl]-3-methyl-7-(2-butyn-1-yl)-8-[(R)-3-tert-butoxycarbonyl-amino-piperidin-1-yl]-xanthine 1c (230 mg, yellow solid), yield: 77.6%.

MS m/z (ES): 582 [M+1]

Step 4: Preparation of 1-[(5-fluoro-1,3-benzothiazol-2-yl)methyl]-3-methyl-7-(2-butyn-1-yl)-8-[(R)-3-amino-piperidin-1-yl]-xanthine The compound 1-[(5-fluoro-1,3-benzothiazol-2-yl)methyl]-3-methyl-7-(2-butyn-1-yl)-8-[(R)-3-tert-butoxycarbonyl-amino-piperidin-1-yl]-xanthine 1c (230 mg, 0.396 mmol) was dissolved in dichloromethane (5 ml). Trifluoroacetic acid (0.7 ml) was added dropwise at room temperature to give a reaction mixture. The reaction mixture was reacted at room temperature for 2 hours, and TLC was used to monitor the reaction progress. After the reaction was completed, the obtained reaction solution was concentrated by using a rotary evaporator at 30° C. to remove trifluoroacetic acid. The residue was dissolved in dichloromethane (5 ml), and potassium carbonate aqueous solution with pH=10 was used to adjust the pH to 7-8, to give a mixed solution. The mixed solution was extracted with dichloromethane and the obtained organic phase was dried over anhydrous magnesium sulfate, and then filtered and concentrated. The residue was separated and purified by thin layer chromatography (dichloromethane:methanol=10:1 as the eluting system) to obtain the compound 1-[(5-fluoro-1,3-benzothiazol-2-yl)methyl]-3-methyl-7-(2-butyn-1-yl)-8-[(R)-3-amino-piperidin-1-yl]-xanthine 1 (153 mg, yellow solid), yield: 80%.

MS m/z (ES): 482 [M+1]

$^1$H NMR (300 MHz, DMSO) δ 8.16-8.03 (m, 1H), 7.87-7.74 (m, 1H), 7.42-7.26 (m, 1H), 5.45 (s, 2H), 4.93 (s, 2H), 3.74-3.53 (m, 2H), 3.41 (s, 3H), 3.14-2.95 (m, 2H), 2.95-2.80 (m, 1H), 1.98-1.73 (m, 5H), 1.72-1.53 (m, 1H), 1.44-1.24 (m, 1H).

Example 2

Preparation of 1-[(1,3-benzothiazol-2-yl)methyl]-3-methyl-7-(2-butyn-1-yl)-8-[(R)-3-amino-piperidin-1-yl]-xanthine Step 1: preparation of 3-methyl-7-(2-butyn-1-yl)-8-bromo-xanthine By utilizing the well known method, 8-bromo-3-methyl-xanthine (5 g, 20.4 mmol) was dissolved in N,N-dimethylformamide (30 ml). N,N-diisopropylethylamine (2.633 g, 20.4 mmol) and 1-bromo-2-butyne (2.714 g, 20.4 mmol) were added to obtain a reaction mixture. The reaction mixture was reacted overnight at room temperature and TLC was used to monitor the reaction progress. After the reaction was completed, the obtained reaction mixture was poured into water, suction filtered, and the obtained solid was washed with water for three times, dried to give 3-methyl-7-(2-butyn-1-yl)-8-bromo-xanthine 1a (5.15 g, light yellow solid), yield: 85%.

MS m/z (ES): 297, 299 [M+1]

Step 2: preparation of 1-[(5-fluoro-1,3-benzothiazol-2-yl)methyl]-3-methyl-7-(2-butyn-1-yl)-8-bromo-xanthine By utilizing the well known method, 3-methyl-7-(2-butyn-1-yl)-8-bromo-xanthine 1a (156 mg, 0.53 mmol) was dissolved in N,N-dimethylformamide (3 ml). 2-bromomethyl-5-fluoro-1,3-benzothiazole (140 mg, 0.57 mmol), potassium carbonate (118 mg, 0.79 mmol) were added to give a reaction mixture. The obtained reaction mixture was reacted overnight at room temperature and TLC was used to monitor the reaction progress. After the reaction was completed, the obtained reaction mixture was poured into water, suction filtered, and the obtained solid was washed with water, dried to give 1-[(5-fluoro-1,3-benzothiazol-2-yl)methyl]-3-methyl-7-(2-butyn-1-yl)-8-bromo-xanthine 1b (240 mg, off-white solid), yield: 99%.

MS m/z (ES): 462, 464 [M+1]

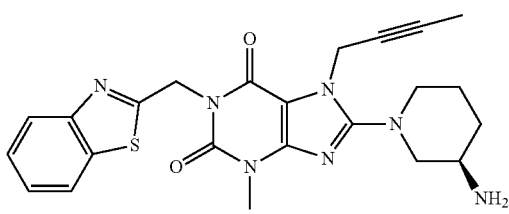 [SMILES: CC#CCn1c(N2CCC[C@@H](N)C2)nc2c1c(=O)n(Cc1nc3ccccc3s1)c(=O)n2C]

Preparation scheme is shown below:

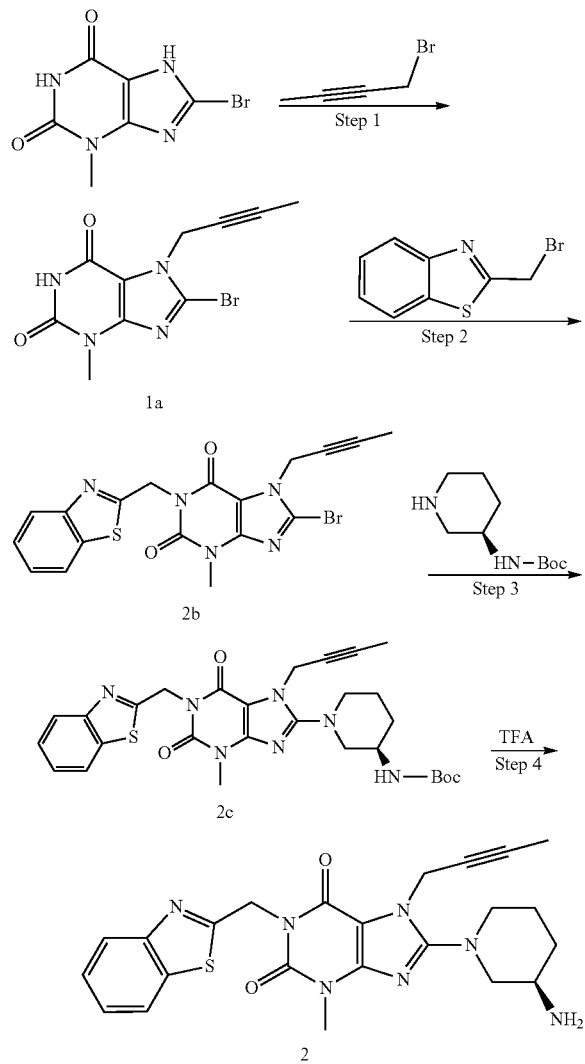

Step 1 was carried out in the same manner as the step 1 in Example 1.

Step 2: Preparation of 1-[(1,3-benzothiazol-2-yl) methyl]-3-methyl-7-(2-butyn-1-yl)-8-bromo-xanthine By utilizing the well known method, 3-methyl-7-(2-butyn-1-yl)-8-bromo-xanthine 1a (327 mg, 1 mmol) was dissolved in N,N-dimethylformamide (5 ml). Potassium carbonate (221 mg, 1.6 mmol) and 2-bromomethyl-1,3-benzothiazole (228 mg, 1 mmol) were added to give a reaction mixture. The reaction mixture was reacted overnight at room temperature and TLC was used to monitor the reaction progress. After the reaction was completed, the obtained reaction mixture was poured into water, suction filtered, and the obtained solid was washed with water, dried to give 1-[(1,3-benzothiazol-2-yl) methyl]-3-methyl-7-(2-butyn-1-yl)-8-bromo-xanthine 2b (400 mg, yellow solid), yield: 90%.

MS m/z (ES): 444, 446 [M+1]

Step 3: Preparation of 1-[(1,3-benzothiazol-2-yl) methyl]-3-methyl-7-(2-butyn-1-yl)-8-[(R)-3-tert-butoxycarbonyl-amino-piperidin-1-yl]-xanthine By utilizing the well known method, 1-[(1,3-benzothiazol-2-yl)methyl]-3-methyl-7-(2-butyn-1-yl)-8-bromo-xanthine 2b (400 mg, 0.9 mmol) was dissolved in N,N-dimethylformamide (6 ml). (R)-3-tert-butoxycarbonyl-aminopiperidine (180 mg, 0.9 mmol) and potassium carbonate (186.5 mg, 1.35 mmol) were added to give a reaction mixture. The reaction mixture was reacted at 75° C. for 2 hours, and TLC was used to monitor the reaction progress. After the reaction was completed, the obtained reaction mixture was cooled to room temperature. The cooled reaction solution was poured into water, suction filtered, and the obtained solid was washed with water, dried to give 1-[(1,3-benzothiazol-2-yl)methyl]-3-methyl-7-(2-butyn-1-yl)-8-[(R)-3-tert-butoxycarbonyl-amino-piperidin-1-yl]-xanthine 2c (460 mg, yellow solid), yield: 90.8%.

MS m/z (ES): 564 [M+1]

Step 4: Preparation of 1-[(1,3-benzothiazol-2-yl) methyl]-3-methyl-7-(2-butyn-1-yl)-8-[(R)-3-amino-piperidin-1-yl]-xanthine By utilizing the well known method, the compound 1-[(1,3-benzothiazol-2-yl)methyl]-3-methyl-7-(2-butyn-1-yl)-8-[(R)-3-tert-butoxycarbonyl-amino-piperidin-1-yl]-xanthine 2c (460 mg, 0.82 mmol) was dissolved in dichloromethane (8 ml). Trifluoroacetic acid (0.8 ml) was added dropwise at room temperature to obtain a reaction mixture. The reaction mixture was reacted at room temperature for 2 hours, and TLC was used to monitor the reaction progress. After the reaction was completed, the obtained reaction mixture was concentrated by using a rotary evaporator at 30° C. to remove trifluoroacetic acid. The residue was dissolved in dichloromethane (5 ml), and potassium carbonate aqueous solution with pH=10 was used to adjust the pH to 7-8, to give a mixed solution. The mixed solution was extracted with dichloromethane and the obtained organic phase was dried over anhydrous magnesium sulfate, and then filtered and concentrated. The residue was separated and purified by thin layer chromatography (dichloromethane:methanol=10:1 as the eluting system) to obtain the compound 1-[(1,3-benzothiazol-2-yl)methyl]-3-methyl-7-(2-butyn-1-yl)-8-[(R)-3-amino-piperidin-1-yl]-xanthine 2 (210 mg, yellow solid), yield: 55.4%.

MS m/z (ES): 464 [M+1]

$^1$H NMR (300 MHz, DMSO) δ 8.04 (d, J=7.7 Hz, 1H), 7.94 (d, J=7.9 Hz, 1H), 7.57-7.35 (m, 2H), 5.45 (s, 2H), 4.91 (s, 2H), 3.75-3.55 (m, 2H), 3.41 (s, 3H), 3.09-2.93 (m, 1H), 2.89-2.70 (m, 2H), 1.92-1.73 (m, 5H), 1.70-1.53 (m, 1H), 1.32-1.15 (m, 1H).

Example 3

Preparation of 1-[(5-chloro-1,3-benzothiazol-2-yl) methyl]-3-methyl-7-(2-butyn-1-yl)-8-[(R)-3-amino-piperidin-1-yl]-xanthine

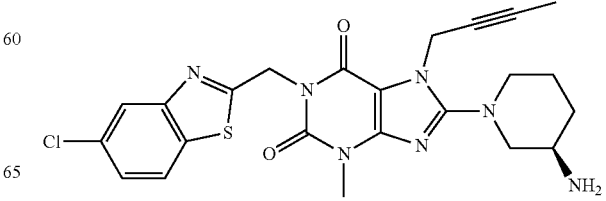

Preparation scheme is shown below:

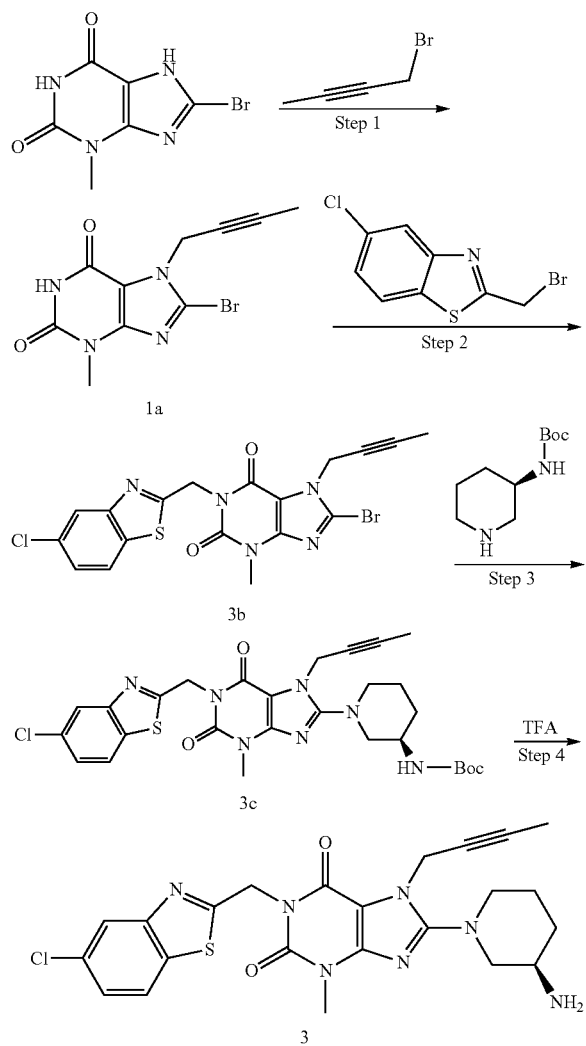

Step 1 was carried out in the same manner as the step 1 in Example 1.

Step 2: preparation of 1-[(5-chloro-1,3-benzothiazol-2-yl)methyl]-3-methyl-7-(2-butyn-1-yl)-8-bromo-xanthine By utilizing the well known method, 3-methyl-7-(2-butyn-1-yl)-8-bromo-xanthine 1a (297 mg, 1 mmol) was dissolved in N,N-dimethylformamide (8 ml). 2-bromomethyl-5-chloro-1,3-benzothiazole (263 mg, 1 mmol) and potassium carbonate (213 mg, 1.5 mmol) were added to give a reaction mixture. The reaction mixture was reacted overnight at room temperature and TLC was used to monitor the reaction progress. After the reaction was completed, the obtained reaction mixture was poured into water, suction filtered, and the obtained solid was washed with water, dried to give 1-[(5-chloro-1,3-benzothiazol-2-yl)methyl]-3-methyl-7-(2-butyn-1-yl)-8-bromo-xanthine 3b (460 mg, light yellow solid), yield: 96%.

MS m/z (ES): 478, 480 [M+1]

Step 3: preparation of 1-[(5-chloro-1,3-benzothiazol-2-yl)methyl]-3-methyl-7-(2-butyn-1-yl)-8-[(R)-3-tert-butoxycarbonyl-aminopiperidin-1-yl]-xanthine By utilizing the well known method, 1-[(5-chloro-1,3-benzothiazol-2-yl)methyl]-3-methyl-7-(2-butyn-1-yl)-8-bromo-xanthine 3b (460 mg, 0.96 mmol) was dissolved in N,N-dimethylformamide (12 ml). (R)-3-tert-butoxycarbonyl-aminopiperidine (193 mg, 0.96 mmol) and potassium carbonate (200 mg, 1.44 mmol) were added to give a reaction mixture. The reaction mixture was reacted at 75° C. for 2 hours, and TLC was used to monitor the reaction progress. After the reaction was completed, the obtained reaction mixture was cooled to room temperature. The cooled reaction solution was poured into cool water, suction filtered, and the obtained solid was washed with water, dried to give 1-[(5-chloro-1,3-benzothiazol-2-yl)methyl]-3-methyl-7-(2-butyn-1-yl)-8-[(R)-3-tert-butoxycarbonyl-amino-piperidin-1-yl]-xanthine 3c (417 mg, grey solid), yield: 72.6%.

MS m/z (ES): 598 [M+1]

Step 4: preparation of 1-[(5-chloro-1,3-benzothiazol-2-yl)methyl]-3-methyl-7-(2-butyn-1-yl)-8-[(R)-3-amino-piperidin-1-yl]-xanthine By utilizing the well known method, 1-[(5-chloro-1,3-benzothiazol-2-yl)methyl]-3-methyl-7-(2-butyn-1-yl)-8-[(R)-3-tert-butoxycarbonyl-amino-piperidin-1-yl]-xanthine 3c (417 mg, 0.7 mmol) was dissolved in dichloromethane (10 ml). Trifluoroacetic acid (1.5 ml) was added dropwise at room temperature to obtain a reaction mixture. The reaction mixture was reacted at room temperature for 2 hours, and TLC was used to monitor the reaction progress. After the reaction was completed, the obtained reaction mixture was concentrated by using a rotary evaporator at 30° C. to remove trifluoroacetic acid. The residue was dissolved in dichloromethane (5 ml), and potassium carbonate aqueous solution with pH=10 was used to adjust the pH to 7-8, to give a mixed solution. The mixed solution was extracted with dichloromethane and the obtained organic phase was dried over anhydrous magnesium sulfate, and then filtered and concentrated. The residue was separated and purified by thin layer chromatography (dichloromethane:methanol=10:1 as the eluting system) to obtain the compound 1-[(5-chloro-1,3-benzothiazol-2-yl)methyl]-3-methyl-7-(2-butyn-1-yl)-8-[(R)-3-amino-piperidin-1-yl]-xanthine 3 (310 mg, light yellow solid), yield: 88.9%.

MS m/z (ES): 498 [M+1]

$^{1}$H NMR (300 MHz, DMSO) δ 8.17-7.98 (m, 2H), 7.54-7.42 (m, 1H), 5.46 (s, 2H), 5.07-4.80 (m, 2H), 3.80-3.48 (m, 2H), 3.41 (s, 3H), 3.19-2.99 (m, 3H), 2.02-1.75 (m, 5H), 1.72-1.59 (m, 1H), 1.57-1.43 (m, 1H).

Example 4

Preparation of 1-[(5-fluoro-1,3-benzothiazol-2-yl)methyl]-3-methyl-7-(2-butyn-1-yl)-8-[(R)-3-amino-piperidin-1-yl]-xanthine hydrochloride

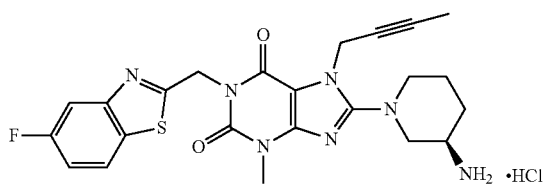 [SMILES: CC#CCn1c(N2CCC[C@@H](N)C2)nc2c1c(=O)n(Cc1nc3cc(F)ccc3s1)c(=O)n2C ; Cl]

Preparation scheme is shown below:

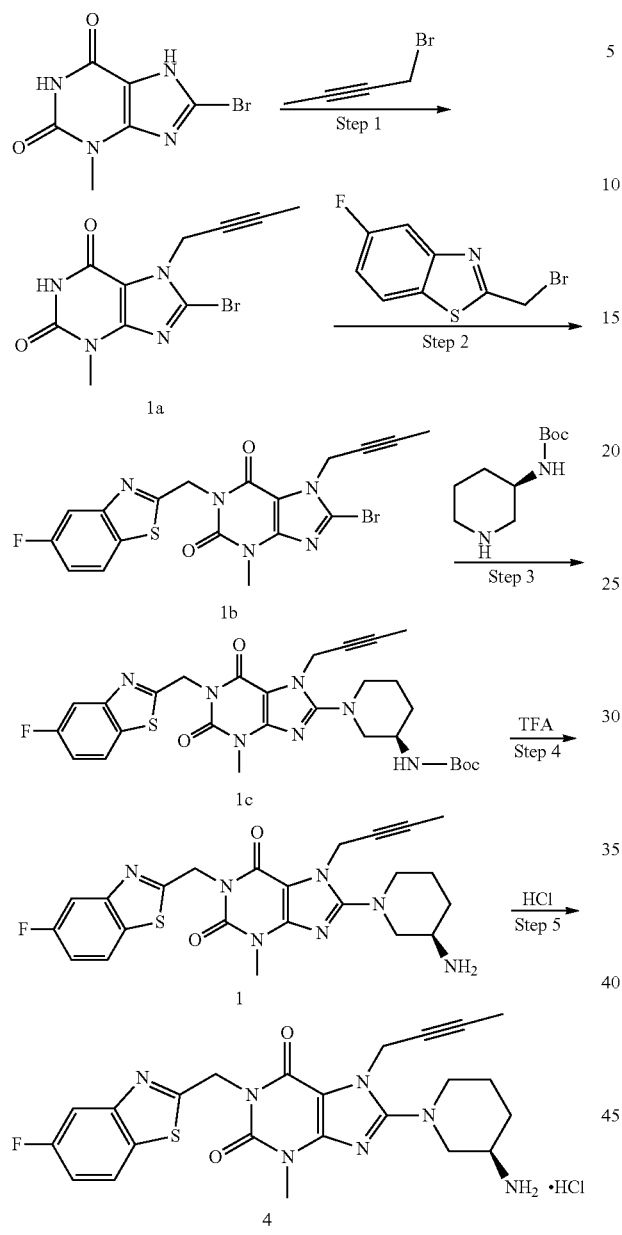

Step 1 was carried out in the same manner as the step 1 in Example 1.
Step 2 was carried out in the same manner as the step 2 in Example 1.
Step 3 was carried out in the same manner as the step 3 in Example 1.
Step 4 was carried out in the same manner as the step 4 in Example 1.

Step 5: preparation of 1-[(5-fluoro-1,3-benzothiazol-2-yl)methyl]-3-methyl-7-(2-butyn-1-yl)-8-[(R)-3-amino-piperidin-1-yl]-xanthine hydrochloride The compound 1-[(5-fluoro-1,3-benzothiazol-2-yl)methyl]-3-methyl-7-(2-butyn-1-yl)-8-[(R)-3-amino-piperidin-1-yl]-xanthine 1 (60 mg, 0.124 mmol) was dissolved in dichloromethane (2 ml). A dichloromethane solution (1 mol/L) of 0.14 ml hydrogen chloride was added to obtain a reaction mixture. The reaction mixture was stirred for 10 minutes, and the solvent was distilled off. The residue was washed with ethyl acetate, and dried, to obtain the target compound 1-[(5-fluoro-1,3-benzothiazol-2-yl)methyl]-3-methyl-7-(2-butyn-1-yl)-8-[(R)-3-amino-piperidin-1-yl]-xanthine hydrochloride 4 (47 mg, yellow solid), yield: 76%.

$^1$H NMR (300 MHz, DMSO) δ 8.55 (s, 3H), 8.09 (dd, J=8.6, 5.4 Hz, 1H), 7.87-7.75 (m, 1H), 7.34 (t, J=8.0 Hz, 1H), 5.46 (s, 2H), 5.14-4.84 (m, 2H), 3.75 (d, J=11.0 Hz, 1H), 3.50 (d, J=12.3 Hz, 1H), 3.42 (s, 4H), 3.23 (dd, J=19.4, 10.9 Hz, 2H), 2.14-1.88 (m, 2H), 1.81 (s, 3H), 1.77-1.62 (m, 2H).

Example 5

Preparation of 1-[(1,3-benzothiazol-2-yl)methyl]-3-methyl-7-(2-butyn-1-yl)-8-[(R)-3-amino-piperidin-1-yl]-xanthine hydrochloride

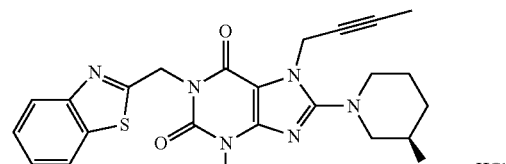

Preparation scheme is shown below:

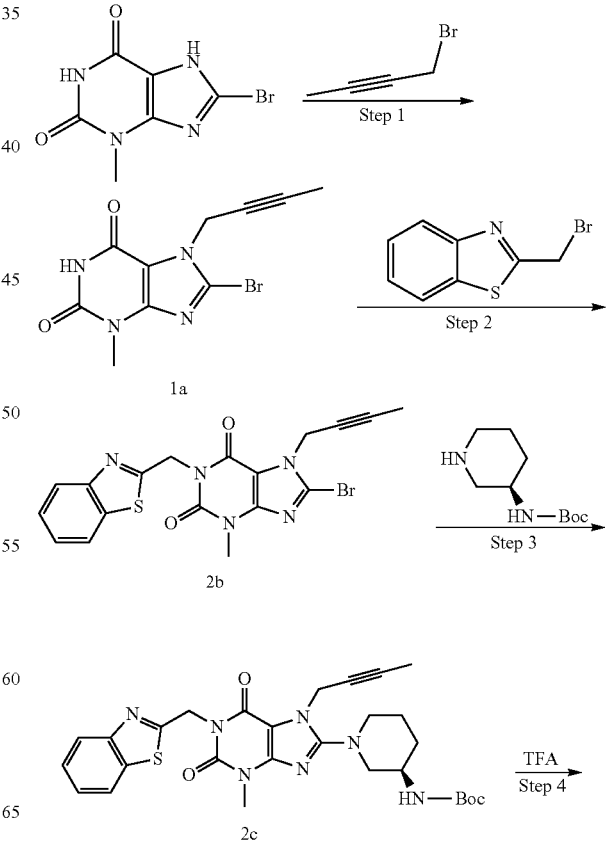

-continued

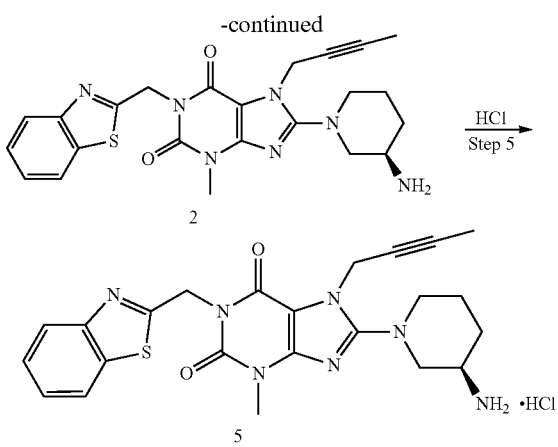

Step 1 was carried out in the same manner as the step 1 in Example 1.

Step 2 was carried out in the same manner as the step 2 in Example 2.

Step 3 was carried out in the same manner as the step 3 in Example 2.

Step 4 was carried out in the same manner as the step 4 in Example 2.

Step 5: preparation of 1-[(1,3-benzothiazol-2-yl)methyl]-3-methyl-7-(2-butyn-1-yl)-8-[(R)-3-amino-piperidin-1-yl]-xanthine hydrochloride The compound 1-[(1,3-benzothiazol-2-yl)methyl]-3-methyl-7-(2-butyn-1-yl)-8-[(R)-3-amino-piperidin-1-yl]-xanthine 2 (100 mg, 0.216 mmol) was dissolved in dichloromethane (3 ml). A dichloromethane solution (1 mol/L) of 0.24 ml hydrogen chloride was added to obtain a reaction mixture. The reaction mixture was stirred for 10 minutes, and the solvent was distilled off. The residue was washed with ethyl acetate, and dried, to obtain the target compound 1-[(1,3-benzothiazol-2-yl)methyl]-3-methyl-7-(2-butyn-1-yl)-8-[(R)-3-amino-piperidin-1-yl]-xanthine hydrochloride 5 (85 mg, yellow solid), yield: 79%.

$^1$H NMR (300 MHz, DMSO) δ 8.47 (s, 3H), 8.05 (d, J=7.7 Hz, 1H), 7.94 (d, J=7.9 Hz, 1H), 7.56-7.34 (m, 2H), 5.46 (s, 2H), 5.11-4.84 (m, 2H), 3.74 (d, J=11.0 Hz, 1H), 3.50 (d, J=11.3 Hz, 1H), 3.42 (s, 4H), 3.31-3.13 (m, 2H), 2.12-1.86 (m, 2H), 1.80 (s, 3H), 1.76-1.60 (m, 2H).

Experimental Example 1

DPP-IV Activity Inhibitory Assay in Vitro

1. The Purpose of the Experiment:

Dipeptidyl peptidase IV (DPP-IV) inhibitory capacities of the compounds prepared in the above-described examples were to be observed, in order to evaluate the inhibitory effect of the compounds prepared in the above-described examples.

2. Experimental Materials:

2.1 Dipeptidyl peptidase IV (DPP-IV): SIGMA products, Item No. D4943-1VL.

2.2 Substrate: Gly-Pro-7-amido-4-methylcoumarin solution, SIGMA products, Item No. G2761-25 mg, FW=41.03.

2.3 DPP-IV buffer: containing 25 mM Hepes, 140 mM NaCl, 1% BSA, 80 mM $MgCl_2$, of which pH was adjusted to 8.0.

2.4 Positive drug (Linagliptin): provided by Shanghai Yingrui Chemical Technology Co., Ltd., specification: 2 g, CAT: YRY0687, LCT#: YR111130, with the molecular weight of 472.54, dissolved in DMSO as a 10 mM stock solution, diluted with distilled water to 10 μM as working solution, with a final concentration of 1 μM.

2.5 Testing equipment: envision (PerkinElmer Company).

3. Experimental Principle:

Gly-Pro-7-amido-4-methylcoumarin can be hydrolyzed by dipeptidyl peptidase IV (DPP-IV) at room temperature, to generate 7-amido-4-methyl coumarin, which can emit fluorescence with wavelength of 460 nm at excitation wavelength of 355 nm. The variation of the product amount can be determined by the variation of fluorescence intensity, so as to reflect the activity level of the enzyme.

4. Experimental Method:

The dipeptidyl peptidase IV (DPP-IV), DPP-IV buffer and test samples were used to construct the reaction system of 200 μL, while the blank control (without enzyme and samples) and negative control (without samples) having the same volume were set up. The reaction system and the controls were reacted at room temperature for 10 min, and then dipeptidyl peptidase IV substrate was added thereto respectively, then reacted at room temperature for 30 min. The fluorescence intensity F (excitation wavelength of 355 nm, emission wavelength of 460 nm) was determined. Inhibition ratio was calculated according to the fluorescence intensity F value, inhibition ratio=$[1-(F_{sample}-F_{blank})/(F_{negative}-F_{blank})]\times 100$. When each of the samples at different concentrations was preliminary screened in duplicate, samples with inhibition ratio of higher than 70% were subjected to false positive exclusion experiments. As for samples confirmed as positive, $IC_{50}$ values thereof were determined, wherein each sample was successively diluted (by 3-fold) to six concentrations, and duplicate was set up for each concentration. According to inhibition ratio, 4 Parameter Logistic Model in Xlfit software was applied to calculate $IC_{50}$.

5. Experimental Results:

The measured $IC_{50}$ data of each compound in the above-described examples of the present invention are as follows:

| Ex. No | Compound | $IC_{50}$ (nM) |
|---|---|---|
| Ex. 1 | | 0.05 |

-continued

| Ex. No | Compound | IC$_{50}$ (nM) |
|---|---|---|
| Ex. 2 | (structure) | 0.10 |
| Ex. 3 | (structure with Cl) | 0.20 |
| Ex. 4 | (structure with F, NH$_2$·HCl) | 0.08 |
| Ex. 5 | (structure with NH$_2$·HCl) | 0.15 |
| Positive control | Linagliptin | 1.00 |

It can be known from the data of DPP-IV activity inhibitory assay in vitro in the above table that, comparing with the positive drug Linagliptin, the compounds in examples of the present invention have significant DPP-IV inhibitory activity.

Experimental Example 2

Impact on Glucose Tolerance in Normal Mice

1. Experimental Material:
1.1 Drugs:
Tool drug: glucose, GC 99.5%, provided by sigma company, Lot No. 101021941, specifications: 100 g/bottle;
Investigational drug: the compound of Example 1, provided by the Synthetic Laboratory of Chengdu Easton Pharmaceutical Co., Ltd., yellow powder, Lot No.: 20120315;
Investigational drug: the compound of Example 2, provided by the Synthetic Laboratory of Chengdu Easton Pharmaceutical Co., Ltd., yellow powder, Lot No.: 20120320;
Investigational drug: the compound of Example 3, provided by the Synthetic Laboratory of Chengdu Easton Pharmaceutical Co., Ltd., light yellow powder, Lot No.: 20120323;
Investigational drug: the compound of Example 4, provided by the Synthetic Laboratory of Chengdu Easton Pharmaceutical Co., Ltd., yellow powder, Lot No.: 20120401;

Positive control: Linagliptin, provided by Shanghai Yingrui Chemical Technology Co., Ltd., specification: 2 g, CAT: YRY0687, LCT#: YR111130.
1.2 Experimental Equipments:
FA2204B electronic balance: provided by Shanghai Precision Instruments Scientific Instrument Co., Ltd.;
METTLER-toledo analytical balance, XS-105 type, provided by Mettler-Toledo company, Swiss;
Blood glucose test strips: ACCU-CHEK active glucose test strips, specification: 50 strips, Lot No.: 23435532, provided by Roche Diagnostics (Shanghai) Co., Ltd;
Surgical scissors, syringes, etc.
1.3 Experimental Animals:
KM mice, 6 weeks old, weighing 18~22 g, half male and half female, 60 mice, provided by Chengdu Dashuo Biological Technology Co., Ltd., Production license: SCXK (Chuan) 2008-24. Animals were housed in the animal room after purchased, adaptively observed for at least three days, and used for assays unless they were qualified for the quarantine standard.
2. Experimental Method:
2.1 Animals were fasted for at least 12 hours before starting the assay;
2.2 Grouping: fasting blood glucose values of the fasted mice were measured, and the mice were randomly grouped according to Table 1, with no significant difference between the groups;

TABLE 1

| Groups | Investigational compounds | Administration route | Drug concentration (mg/ml) | Volume of administration (ml/10 g) | Dosage of administration (mg/kg) | Dosage of glucose (g/kg) |
|---|---|---|---|---|---|---|
| Ex.1 group | Compound of Ex.1 | i.g | 0.15 | 0.2 | 3 | 8 |
| Ex.2 group | Compound of Ex. 2 | i.g | 0.15 | 0.2 | 3 | 8 |
| Ex.3 group | Compound of Ex. 3 | i.g | 0.15 | 0.2 | 3 | 8 |
| Ex.4 group | Compound of Ex. 4 | i.g | 0.15 | 0.2 | 3 | 8 |
| Positive group | Linagliptin | i.g | 0.15 | 0.2 | 3 | 8 |
| Blank group | normal saline | i.g | — | 0.2 | — | 8 |

2.3 Measurement of Blood Glucose Value:

Animals in each group were administrated with corresponding investigational compounds according the Table 1 by intragastric administration (i.g), then administrated with glucose (8 g/kg) respectively by intragastric administration at 30 min after administrating drugs, and the blood glucose values thereof were measured respectively at 30 min, 60 min and 120 min after administrating the glucose (glucose loaded).

3. Statistical Method:

Excel was used for statistics, experimental data were expressed as ($\bar{x}\pm SD$), and two-sided T-test method was used to statistically compare the experimental data among multiple groups.

4. Experimental Results

TABLE 2

| Groups | Dosage (mg/kg) | Fasting blood glucose (mmol/L) | blood glucose at 30 min after glucose loaded (mmol/L) | blood glucose at 60 min after glucose loaded (mmol/L) | blood glucose at 120 min after glucose loaded (mmol/L) |
|---|---|---|---|---|---|
| Blank group | — | 7.12 ± 1.08 | 24.86 ± 2.06 | 21.86 ± 1.52 | 11.98 ± 0.90 |
| Positive group | 3 | 7.13 ± 0.86 | 17.07 ± 1.83** | 14.98 ± 1.66** | 9.96 ± 0.89** |
| Ex. 1 group | 3 | 7.27 ± 0.74 | 15.02 ± 1.99**▲▲ | 12.61 ± 1.98**▲▲ | 8.79 ± 0.88**▲▲ |
| Ex. 2 group | 3 | 7.43 ± 1.32 | 15.59 ± 2.04**▲ | 12.78 ± 1.97**▲ | 8.96 ± 1.16**▲ |
| Ex. 3 group | 3 | 7.19 ± 1.04 | 15.61 ± 1.10**▲ | 13.49 ± 1.31**▲ | 8.90 ± 1.26**▲ |
| Ex. 4 group | 3 | 7.25 ± 0.98 | 15.50 ± 1.94**▲ | 12.75 ± 1.43**▲ | 8.91 ± 0.98**▲ |

Note:
compared with the blank group, *P < 0.05, **P < 0.01;
compared with positive group, ▲P < 0.05, ▲▲P < 0.01.

5. Conclusions (1) It can be seen from Table 2 that, compared with the blank group, at 30 min, 60 min and 120 min after glucose loaded, the blood glucose values in the Ex. 1 group, the Ex. 2 group, the Ex. 3 group, the Ex. 4 group and the positive group have significant difference (**P<0.01), showing that all of the compound of Example 1, the compound of Example 2, the compound of Example 3, the compound of Example 4 and the positive drug (Linagliptin) can extremely significantly decrease the blood glucose levels;

(2) Compared with the positive drug (Linagliptin), at 30 min, 60 min and 120 min after glucose loaded, the blood glucose value in the Ex. 1 group extremely significantly decreased (▲▲P<0.01), while the blood glucose value in the Ex. 2 group, that in the Ex. 3 group, and that in the Ex. 4 group significantly decreased (▲P<0.05), showing that hypoglycemic effects of compounds in the Examples of the present invention are remarkable.

Experimental Example 3

Impact on Blood Glucose in Spontaneous Diabetic Mice

1. Experimental Materials:
1.1 Drugs:

Tool drug: glucose, GC 99.5%, provided by sigma company, Lot No. 101 021 941, specifications: 100 g/bottle;

Investigational drug: the compound of Example 1, provided by the Synthetic Laboratory of Chengdu Easton Pharmaceutical Co., Ltd., yellow powder, Lot No.: 20120315;

Investigational drug: the compound of Example 2, provided by the Synthetic Laboratory of Chengdu Easton Pharmaceutical Co., Ltd., yellow powder, Lot No.: 20120320;

Investigational drug: the compound of Example 3, provided by the Synthetic Laboratory of Chengdu Easton Pharmaceutical Co., Ltd., light yellow powder, Lot No.: 20120323;

Investigational drug: the compound of Example 4, provided by the Synthetic Laboratory of Chengdu Easton Pharmaceutical Co., Ltd., yellow powder, Lot No.: 20120401;

Positive control: Linagliptin, provided by Shanghai Yingrui Chemical Technology Co., Ltd., specification: 2 g, CAT: YRY0687, LCT#: YR111130.

1.2 Experimental Equipments:

FA2204B electronic balance: provided by Shanghai Precision Instruments Scientific Instrument Co., Ltd.;

METTLER-toledo analytical balance, XS-105 type, provided by Mettler-Toledo company, Swiss;

Blood glucose test strips: ACCU-CHEK active glucose test strips, specification: 50 strips, Lot No.: 23435532, provided by Roche Diagnostics (Shanghai) Co., Ltd;

Surgical scissors, syringes, etc.

1.3 Experimental Animals:

Type II spontaneous diabetic KKAy obese mice, 60 mice, 14 weeks old, half male and half female, purchased from Institute of Laboratory Animal Science, Chinese Academy of Medical Sciences (Qualified number: SCXK (Jing) 2009-0004). Animals were housed in the animal room after purchased, adaptively observed for at least three days, and used for assays unless they were qualified for the quarantine standard.

2. Experimental Method:

2.1 Animals were fasted for at least 12 hours before starting the assay;

2.2 Fasting blood glucose values of the fasted mice were measured by ACCU-CHEK active glucose test strips, and the mice were randomly grouped according to Table 3. In addition, the C57BL/6J mice were used for the blank control group, while the type II spontaneous diabetic KKAy mice were used for the model group.

TABLE 3 assay grouping and dosing regimen

| Groups | Investigational compounds | Administration route | Drug concentration (mg/ml) | Volume of administration (ml/10 g) | Dosage of administration (mg/kg) | Dosage of glucose (g/kg) |
|---|---|---|---|---|---|---|
| Blank control group | normal saline | i.g | — | 0.2 | — | 8 |
| Ex.1 group | Compound of Ex.1 | i.g | 0.15 | 0.2 | 3 | 8 |
| Ex.2 group | Compound of Ex. 2 | i.g | 0.15 | 0.2 | 3 | 8 |
| Ex.3 group | Compound of Ex. 3 | i.g | 0.15 | 0.2 | 3 | 8 |
| Ex.4 group | Compound of Ex. 4 | i.g | 0.15 | 0.2 | 3 | 8 |
| Positive group | Linagliptin | i.g | 0.15 | 0.2 | 3 | 8 |
| Model group | normal saline | i.g | — | 0.2 | — | 8 |

2.3 Measurement of Blood Glucose Value:

Animals in each group were administrated with corresponding investigational compounds according Table 3 by intragastric administration (i.g), then administrated with glucose (8 g/kg) respectively by intragastric administration at 30 min after administrating drugs, and the blood glucose values thereof were measured respectively at 30 min, 60 min and 120 min after administrating the glucose (glucose loaded).

3. Statistical Method:

Excel was used for statistics, experimental data were expressed as ($\bar{x} \pm SD$), and two-sided T-test method was used to statistically compare the experimental data among multiple groups.

4. Experimental Results

TABLE 4

Impact on glucose tolerance in spontaneous diabetic mice ($\bar{x} \pm SD$)

| Groups | Dosage (mg/kg) | Fasting blood glucose (mmol/L) | blood glucose at 30 min after glucose loaded (mmol/L) | blood glucose at 60 min after glucose loaded (mmol/L) | blood glucose at 120 min after glucose loaded (mmol/L) |
|---|---|---|---|---|---|
| Blank group | — | 7.96 ± 0.88 | 19.63 ± 1.96 | 15.76 ± 1.82 | 11.35 ± 1.74 |
| Model group | — | 9.31 ± 0.50* | 25.18 ± 2.40** | 18.79 ± 1.54** | 14.22 ± 1.97** |
| Positive group | 3 | 9.09 ± 0.53* | 17.14 ± 1.45▲▲ | 13.10 ± 1.38▲▲ | 11.27 ± 1.43▲▲ |
| Ex. 1 group | 3 | 9.29 ± 0.71* | 14.98 ± 1.53▲▲★ | 11.10 ± 2.45▲▲▲ | 9.97 ± 1.28▲▲ |
| Ex. 2 group | 3 | 9.07 ± 0.67* | 15.59 ± 1.23▲▲★ | 11.41 ± 1.58▲▲▲ | 10.81 ± 1.37▲▲ |
| Ex. 3 group | 3 | 9.15 ± 0.61* | 15.86 ± 1.04▲▲★ | 11.28 ± 1.67▲▲▲ | 10.73 ± 1.46▲▲ |

TABLE 4-continued

Impact on glucose tolerance in spontaneous diabetic mice ($\bar{x} \pm SD$)

| Groups | Dosage (mg/kg) | Fasting blood glucose (mmol/L) | blood glucose at 30 min after glucose loaded (mmol/L) | blood glucose at 60 min after glucose loaded (mmol/L) | blood glucose at 120 min after glucose loaded (mmol/L) |
|---|---|---|---|---|---|
| Ex. 4 group | 3 | 9.17 ± 0.58* | 15.60 ± 1.30▲▲★ | 11.45 ± 1.60▲▲★ | 10.75 ± 1.20▲▲ |

Note:
compared with the blank group, *P < 0.05, **P < 0.01;
compared with the model group, ▲P < 0.05, ▲▲P < 0.01;
compared with the positive group, ★P < 0.05, ★★P < 0.01.

5. Conclusion (1) It can be seen from Table 4 that, compared with the blank group, both of the fasting blood glucose value and the blood glucose value after glucose loaded in the model group were significantly increased (*P<0.05, **P<0.01), showing that the spontaneous diabetic mice model was stable;

(2) Compared with the model group, at 30 min, 60 min and 120 min after glucose loaded, the blood glucose values in every drug administration groups significantly decreased (▲▲P<0.01), showing that all of the compounds of Examples 1-4 and the positive drug Linagliptin can extremely significantly decrease the blood glucose levels;

(3) Compared with the positive drug Linagliptin, at 30 min after glucose loaded, the blood glucose value in the Ex. 1 group extremely significantly decreased (★★P<0.01), while the blood glucose value in the Ex. 2 group, that in the Ex. 3 group, and that in the Ex. 4 group significantly decreased (★P<0.05); at 60 min after glucose loaded, the blood glucose values in every example groups significantly decreased (★P<0.05), showing that hypoglycemic effects of compounds in examples of the present invention are remarkable.

The above results indicate that, the compounds in the Examples of the present invention exhibit significant DPP-IV inhibitory activity and hypoglycemic effect.

It is apparent for the ordinary skilled in the art that, without departing from the spirit or scope of the present invention, various modifications and variations can be made to the compounds, compositions and the preparation methods of the present invention, therefore, the protection scope of the present invention covers various modifications and variations made thereto, as long as the modifications and variations fall within the scope encompassed by the claims and equivalent embodiments thereof.

What is claimed is:

1. A compound as shown in formula I or a pharmaceutically acceptable salt thereof:

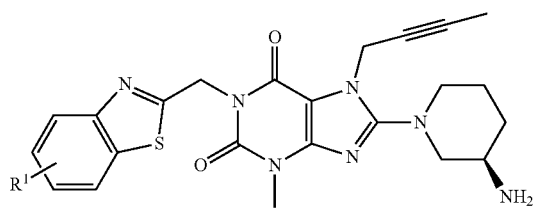

(I)

wherein: $R^1$ is selected from hydrogen atom, fluorine atom, chlorine atom, bromine atom, iodine atom or cyano group.

2. The compound or a pharmaceutically acceptable salt thereof according to claim 1, characterized in that $R^1$ is substituted at the 5-position of (1,3-benzothiazol-2-yl)methyl.

3. The compound or a pharmaceutically acceptable salt thereof according to claim 1, characterized in that $R^1$ is selected from hydrogen atom, fluorine atom or chlorine atom.

4. The compound or a pharmaceutically acceptable salt thereof according to claim 1, characterized in that the compound is:

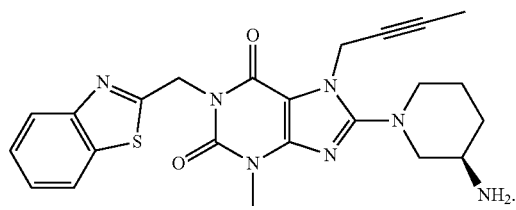 [SMILES: CC#CCn1c(N2CCC[C@@H](N)C2)nc2c1c(=O)n(Cc1nc3ccccc3s1)c(=O)n2C]

5. The compound or a pharmaceutically acceptable salt thereof according to claim 1, characterized in that the compound is:

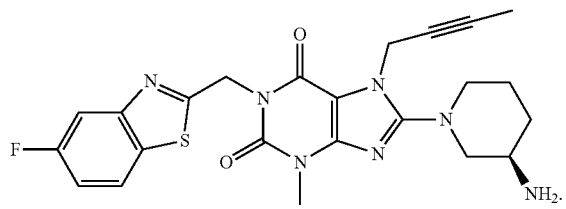 [SMILES: CC#CCn1c(N2CCC[C@@H](N)C2)nc2c1c(=O)n(Cc1nc3cc(F)ccc3s1)c(=O)n2C]

6. The compound or a pharmaceutically acceptable salt thereof according to claim 1, characterized in that the compound is:

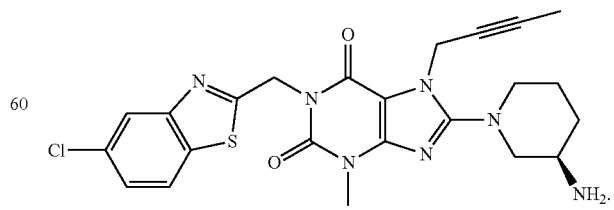

7. The compound or a pharmaceutically acceptable salt thereof according to claim 1, characterized in that the pharmaceutically acceptable salt is formed by the compound and an acid selected from: hydrochloric acid, p-toluenesulfonic acid, tartaric acid, maleic acid, lactic acid, methanesulfonic acid, sulfuric acid, phosphoric acid, citric acid, acetic acid or trifluoroacetic acid.

8. The compound or a pharmaceutically acceptable salt thereof according to claim 7, characterized in that the acid is p-toluenesulfonic acid, hydrochloric acid, tartaric acid or trifluoroacetic acid.

9. The compound or a pharmaceutically acceptable salt thereof according to claim 1, characterized in that the compound or the pharmaceutically acceptable salts thereof is:
- 1-[(5-fluoro-1,3-benzothiazol-2-yl)methyl]-3-methyl-7-(2-butyn-1-yl)-8-[(R)-3-amino-piperidin-1-yl]-xanthine;
- 1-[(1,3-benzothiazol-2-yl)methyl]-3-methyl-7-(2-butyn-1-yl)-8-[(R)-3-amino-piperidin-1-yl]-xanthine;
- 1-[(5-chloro-1,3-benzothiazol-2-yl)methyl]-3-methyl-7-(2-butyn-1-yl)-8-[(R)-3-amino-piperidin-1-yl]-xanthine;
- 1-[(5-fluoro-1,3-benzothiazol-2-yl)methyl]-3-methyl-7-(2-butyn-1-yl)-8-[(R)-3-amino-piperidin-1-yl]-xanthine hydrochloride; or
- 1-[(1,3-benzothiazol-2-yl)methyl]-3-methyl-7-(2-butyn-1-yl)-8-[(R)-3-amino-piperidin-1-yl]-xanthine hydrochloride.

10. A preparation method of the compound or a pharmaceutically acceptable salt thereof according to claim 1, comprising the following steps:

Step 1: at room temperature, a starting raw material a is reacted with a raw material A to give an intermediate b;

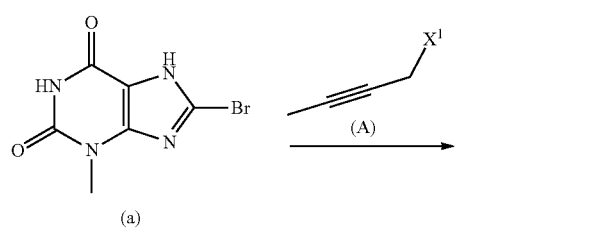

wherein, in the raw material A, $X^1$ is a leaving group;

Step 2: at room temperature, the intermediate b is further subjected to a substitution reaction with a raw material B to give an intermediate c;

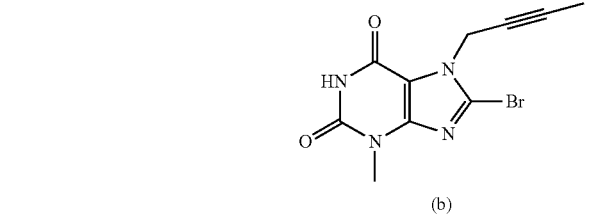

wherein, in the raw material B, $X^2$ is a leaving group;

Step 3: under heating condition, the obtained intermediate c is reacted with (R)-3-tert-butoxycarbonyl aminopiperidine, to give an intermediate d;

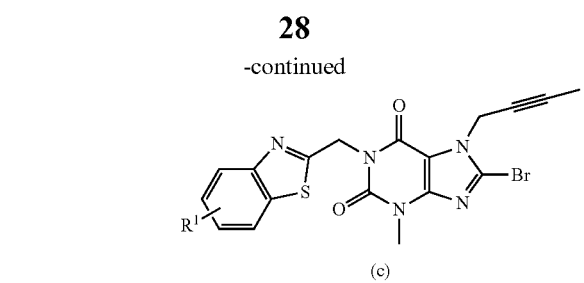

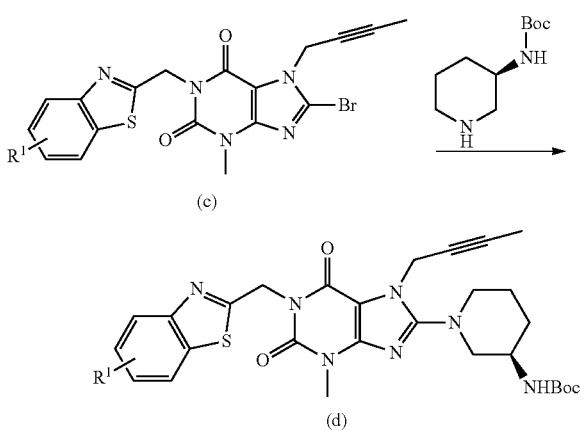

Step 4: at room temperature, the obtained intermediate d is subjected to deprotection under acid condition, to give the target compound I as a free base;

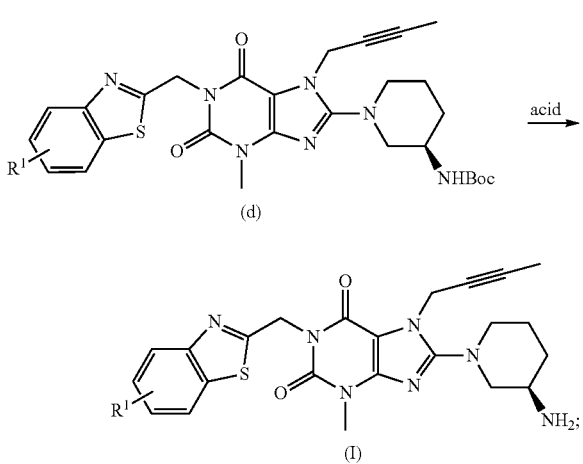

and

Step 5, as an optional step: at room temperature, the obtained target compound I is further reacted with an acid (HA), to prepare the corresponding salt e;

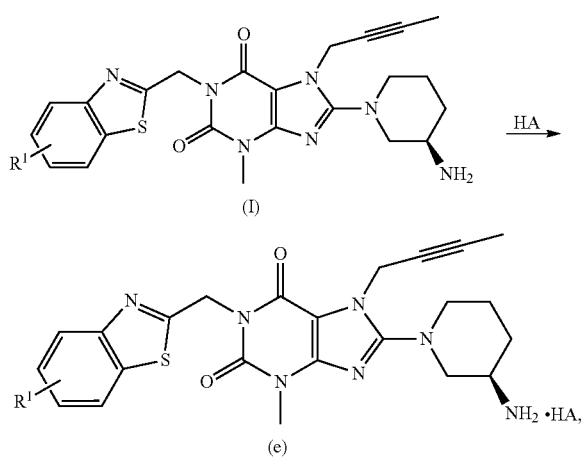

and
R1 is defined in claim 1.

11. A method for treating dipeptidyl peptidase IV related diseases comprising administering a compound or a pharmaceutically acceptable salt thereof of claim 1 to a subject in need thereof, wherein the dipeptidyl peptidase IV related disease is type II diabetes or diseases of abnormal glucose tolerance.

12. The method of claim 10, $X^1$ is Cl, Br or I.

13. The method of claim 10, wherein $X^2$ is Cl, Br or I.

14. The method of claim 10, wherein the acid in step 4 is hydrochloric acid or trifluoroacetic acid.

15. The method of claim 10, wherein the acid in step 5 is p-toluenesulfonic acid, hydrochloric acid, tartaric acid or trifluoroacetic acid.

16. The method of claim 10, wherein said room temperature is 10-25° C.

17. The method of claim 10, wherein said heating condition is 50-100° C.

* * * * *